(12) United States Patent
Lee et al.

(10) Patent No.: US 7,307,259 B2
(45) Date of Patent: Dec. 11, 2007

(54) SYSTEM AND METHOD FOR CONTROLLING COMPOSITION FOR LITHOGRAPHY PROCESS IN REAL TIME USING NEAR INFRARED SPECTROMETER

(75) Inventors: Ki-Beom Lee, Kyungki-Do (KR); Jae-Ku Lee, Kyungki-Do (KR); Mi-Sun Park, Kyungki-Do (KR); Jong-Min Kim, Kyungki-Do (KR); Min-Gun Lee, Kyungki-Do (KR)

(73) Assignee: Dongjin Semichem Co., Ltd., Incheon (KR)

( * ) Notice: Subject to any disclaimer, the term of this patent is extended or adjusted under 35 U.S.C. 154(b) by 328 days.

(21) Appl. No.: 11/075,806

(22) Filed: Mar. 10, 2005

(65) Prior Publication Data

US 2005/0202564 A1    Sep. 15, 2005

(30) Foreign Application Priority Data

Mar. 11, 2004    (KR) ...................... 10-2004-0016638

(51) Int. Cl.
*G01J 5/02*    (2006.01)
(52) U.S. Cl. .................................. 250/343; 250/339.11
(58) Field of Classification Search ........... 250/339.11, 250/339.12, 341.8, 343; 438/704, 745
See application file for complete search history.

(56) References Cited

U.S. PATENT DOCUMENTS 7,127,358 B2 * 10/2006 Yue et al. ...................... 702/30

2003/0138710 A1 *  7/2003 Park et al. ..................... 430/30
2003/0235997 A1 * 12/2003 Lee et al. ................... 438/745
2004/0180269 A1 *  9/2004 Balasubramaniam et al. .. 430/5

* cited by examiner

Primary Examiner—David Porta
Assistant Examiner—David S Baker
(74) Attorney, Agent, or Firm—Birch, Stewart, Kolasch & Birch, LLP

(57) ABSTRACT

A system and a method for controlling the multi-component composition such as photoresist, stripper, developer, etchant, thinner, rinser/cleaner and etch bead remover, for a lithography process, which is used for manufacturing a semiconductor device, a liquid crystal display device and so on, are disclosed. The system includes a composition circulator for withdrawing the composition from a storage tank retaining the composition for a lithography process, and for recycling the withdrawn composition to the storage tank, through a flow cell; a composition analyzer for measuring an absorbance of the composition passing through the flow cell, and for calculating the concentration of at least one component of the composition from the measured absorbance; a component supplier for supplying a deficient component to the storage tank when a concentration of the deficient component is below a predetermined level; and a controller for controlling the component supplier to adjust the concentration of each component of the composition according to the absorbance.

8 Claims, 4 Drawing Sheets

SYSTEM AND METHOD FOR CONTROLLING COMPOSITION FOR LITHOGRAPHY PROCESS IN REAL TIME USING NEAR INFRARED SPECTROMETER

FIELD OF THE INVENTION

This invention relates to a system and a method for controlling the composition for lithography process in real time using a near infrared spectrometer. More particularly, this invention relates to a system and a method for automatically controlling the multi-component composition, such as photoresist, stripper, developer, etchant, thinner, rinser/cleaner and EBR (etch bead remover), which is used in a lithography process for manufacturing a semiconductor device, a liquid crystal display device (LCD) and so on, in real time (on-line) using a near infrared spectrometer.

BACKGROUNDS OF THE INVENTION

The composition, such as photoresist, stripper, developer, etchant, thinner, rinser/cleaner, EBR (etch bead remover) and so on, is conventionally used in a lithography process for manufacturing a semiconductor device, a LCD device and so on. The composition contains various components such as organic solvent, photoresist component, water, acid component, base component, and so on. As the apparatus for analyzing these components in the composition, a titroprocessor, an ion chromatography, a gas chromatography, a capillary ion analyzer, a moisture analyzer, a UV-Vis spectrometer, a Raman spectrometer and so on are conventionally used. However, it usually takes too much time to analyze the various components in the composition with the conventional apparatuses. In order to reduce the time required for analyzing the various components, more than two apparatuses can be used at the same time. However, even in that case, the real-time analysis of each component cannot be carried out adequately, and therefore it is not easy to improve the time efficiency for analysis. Furthermore, it is difficult to avoid problem when analyzing the compositions with the conventional apparatuses.

In order to overcome these disadvantages, the method of using an on-line analysis apparatus has been recently developed. However, the present on-line analysis apparatus only performs an automatic sampling, and accordingly cannot sufficiently reduce the required time for analysis, and cannot analyze the various components in real time and at the same time. Namely, it is impossible to obtain the overall information of the analyzed composition in real time, which is required for handling or controlling the composition used in a lithography process. Accordingly, it is required the method, which can analyze in real time the components of the composition used in a lithography process for manufacturing a semiconductor and an LCD device, and which can control the lifespan of the composition, and manage and recycle the composition.

SUMMARY OF THE INVENTION

Accordingly, it is an object of the present invention to provide a system and a method for controlling the composition for a lithography process in real time using a near infrared spectrometer, which can analyze and control the components such as organic solvent, photoresist component, water, acid component and base component, which is included in the composition for the lithography process, such as photoresist, stripper, developer, etchant, thinner, rinser/cleaner and EBR (etch bead remover).

It is other object of the present invention to provide a system and a method for controlling the composition for a lithography process, which is capable of simply sampling the multi-component composition for the lithography process.

It is another object of the present invention to provide a system and a method for controlling the composition for a lithography process, which can improve the process efficiency by transferring or adding a necessary composition with a pump or a vacuum apparatus according to the properties of the composition.

It is another object of the present invention to provide a system and a method for controlling the composition for a lithography process, which can analyze the multi-component composition without causing any change or degradation in the component thereof, and can reuse or recycle the analyzed composition, and reduce the generation of waste water.

To achieve these and other objects, the present invention provides a system for controlling a composition for a lithography process in real time, which comprises a composition circulator for withdrawing the composition from a storage tank retaining the composition for a lithography process, and for recycling the withdrawn composition to the storage tank, through a flow cell; a composition analyzer for measuring an absorbance of the composition passing through the flow cell, and for calculating the concentration of at least one component of the composition from the measured absorbance; a component supplier for supplying a deficient component to the storage tank when a concentration of the deficient component is below a predetermined level; and a controller for controlling the component supplier to adjust the concentration of each component of the composition according to the absorbance.

The present invention provides a method for controlling a composition for a lithography process in real time, which comprises the steps of; transferring a composition in a storage tank for a lithography process to a transfer vessel of a depressurized condition; transferring the composition in the transfer vessel to a flow cell by injecting inert gas to the transfer vessel; measuring a concentration of at least one component of the composition by measuring an absorbance of the composition while the composition passes through the flow cell; recycling the composition from the flow cell to the storage tank; transferring a deficient component of the composition into an addition tank; and supplying the deficient component in the addition tank into the storage tank.

BRIEF DESCRIPTION OF THE DRAWINGS

A more complete appreciation of the invention, and many of the attendant advantages thereof, will be better understood by reference to the following drawings, wherein.

DETAILED DESCRIPTION OF THE INVENTION

Preferred embodiments of the present invention will be explained in the following detailed description by reference to the accompanying drawings.

Figure 1:
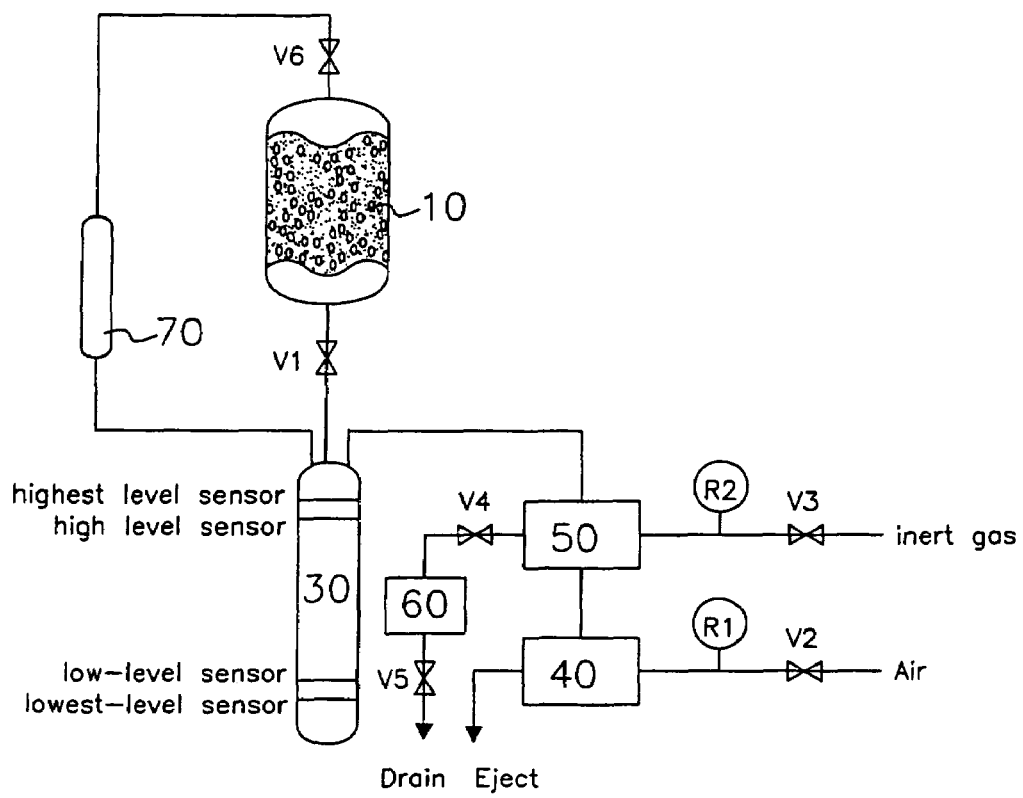
FIG. 1 is a block diagram of a composition circulator, which is used in a system for controlling a composition for a lithography process in real time using a near infrared spectrometer according to an embodiment of the present invention.

The system for controlling the composition for a lithography process in real time according to the present invention comprises i) a composition circulator, iii) a composition analyzer, iii) a component supplier and iv) a controller. FIG. 1 is a block diagram of the composition circulator according to an embodiment of the present invention. As shown in FIG. 1, the composition circulator comprises the first automatic valve V1, which is installed on a storage tank 10 retaining the composition for a lithography process, and is used for withdrawing the composition from the storage tank 10; a transfer vessel 30 for receiving the composition withdrawn from the storage tank 10 through the first automatic valve V1, and for transferring the received composition to a flow cell 70; and a vacuum reservoir 50 for vacuumizing the transfer vessel 30. The vacuum reservoir 50 is vacuumized or is supplied with inert gas such as nitrogen gas. When the vacuum reservoir 50 is vacuumized, the composition is supplied to the transfer vessel 30 from the storage tank 10. When inert gas is supplied to the vacuum reservoir 50, the composition is transferred to the flow cell 70 from the transfer vessel 30 due to the pressure of the inert gas, and then the analyzed composition in the flow cell 70 is recycled to the storage tank 10 through the sixth automatic valve V6.

The composition circulator can further include a vacuum ejector 40 for vacuumizing the vacuum reservoir 50 by receiving air and ejecting air therefrom according to the control of the second automatic valve V2. The amount of a ir injected into the vacuum ejector 40 can be adjusted by the first regulator R1 installed between the second automatic valve V2 and the vacuum ejector 40. Also, the composition circulator can further include a drain transfer tank 60, which is connected to the vacuum reservoir 50, for receiving the composition overflowing from the transfer vessel 30 when the excess amount of the composition is injected into the transfer vessel 30, and also can further include the fourth automatic valve V4 for controlling the composition's flow into the drain transfer tank 60, the fifth automatic valve V5 for controlling the composition's ejection from the drain transfer tank 60, the third automatic valve V3 for injecting inert gas (nitrogen gas) to the vacuum reservoir 50 and the second regulator R2 for controlling the a mount of nitrogen gas injected into the vacuum reservoir 50.

Figure 2:
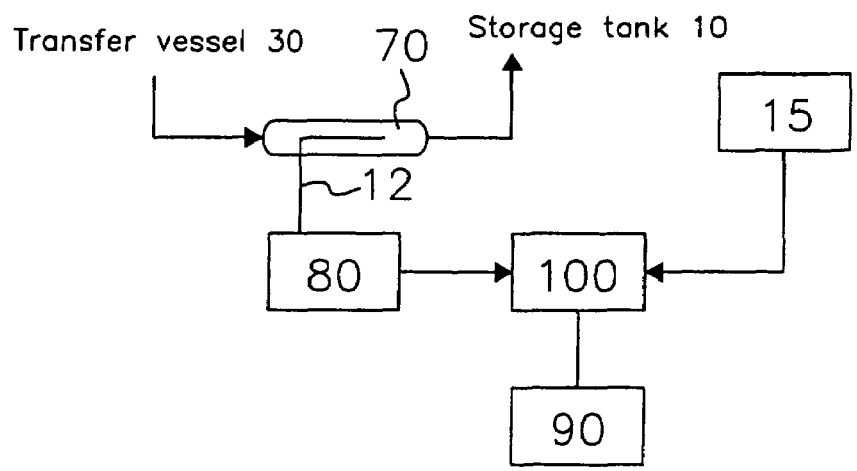
FIG. 2 is a block diagram of a composition analyzer and a controller, which are used in a system for controlling a composition according to an embodiment of the present invention.

FIG. 2 is a block diagram of the composition analyzer and the controller. As shown in FIG. 2, ii) the composition analyzer includes the flow cell 70, through which the composition to be analyzed passes, an optical fiber 12 for irradiating light to the composition for measuring absorbance of the composition, and a near infrared spectrometer 80 for measuring the absorbance of the composition. When the composition is transferred to the flow cell 70 from the transfer vessel 30, the light from the near infrared spectrometer 80 is irradiated to the composition through the optical fiber 12. The near infrared spectrometer 80 measures the absorbance of the composition passing through the flow cell 70, and calculates the concentration of at least one component thereof from the measured absorbance, and then transmits the information about the concentration to the controller 100. The controller 100 outputs the information about the concentration of the component through an output unit 90, together with the composition's status such as the "used time" and the "number of use in a lithography process", which is transmitted from a tank controller 15. The controller 100 also controls the component supplier to adjust the concentration of each component of the composition, according to the analyzed results of the composition.

Figure 3:
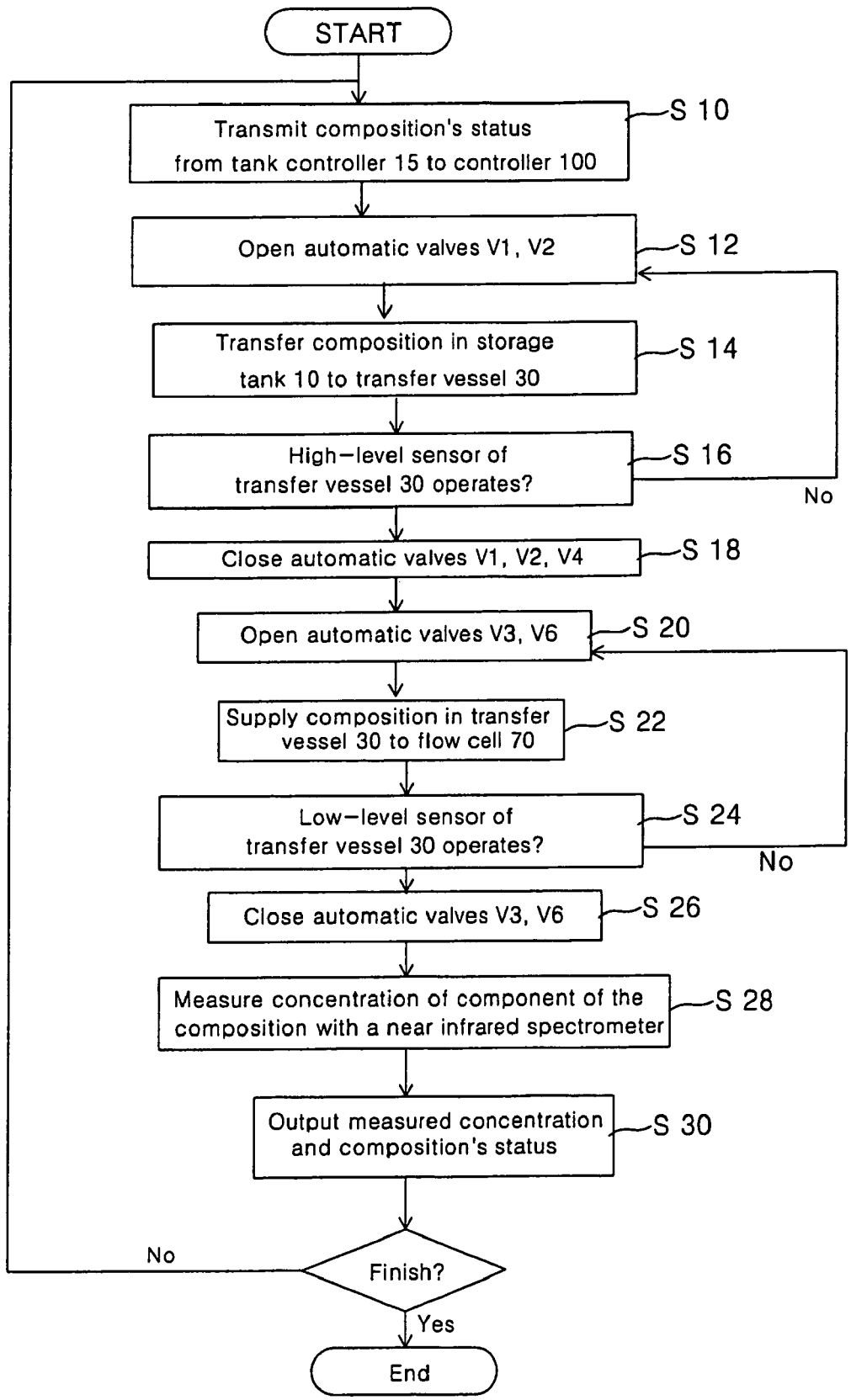
FIG. 3 is a flow chart for illustrating the operation of a composition circulator, a composition analyzer and a controller, which are used in a system for controlling a composition according to an embodiment of the present invention.

By reference to FIG. 3, the operation of i) the composition circulator, ii) the composition analyzer and iv) the controller are explained hereinafter. As shown in FIG. 3, in order to transfer and analyze the composition in the storage tank 10, firstly, the information about the composition's status such as the "used time" and the "number of use in a lithography process", is transmitted from the tank controller 15 to the controller 100 (S10). Then, the first automatic valve V1, which is connected to the storage tank 10 being currently used, and the second automatic valve V2, which is connected to the vacuum ejector 40, are opened (S12). When the second automatic valve V2 is opened, the vacuum ejector 40 is vacuumized, and the vacuum reservoir 50 and the transfer vessel 30 are depressurized, and consequently the composition in the storage tank 10 is transferred to the transfer vessel 30 of depressurized condition through the first automatic valve V1(S14). In that case, the degree of vacuumization of the vacuum ejector 40 can be adjusted by controlling the amount of the injected air by controlling the first regulator R1 connected to air injection inlet. According to the degree of vacuumization, the composition is transferred into the transfer vessel 30 slowly or fast. When the excess amount of the composition is injected to the transfer vessel 30, the excess amount can be ejected therefrom to the drain transfer tank 60 by opening the second and forth automatic valves V2, V4 simultaneously. When the excess amount is injected to the drain transfer tank 60, the state is detected by a sensor (not shown), and the third, fourth and fifth automatic valves V3, V4, V5 are opened, and nitrogen gas is injected. Therefore, the composition in the drain transfer tank 60 is ejected therefrom by the pressure of nitrogen gas.

When the composition is transferred to the transfer vessel 30 from the storage tank 10, a lowest-level sensor and a low-level sensor in the transfer vessel 30 operates successively. When the composition is continuously transferred into the transfer vessel 30, a high-level sensor operates (S 16), and the first, second and fourth automatic valves V1, V2, V4 are closed (S 18). Then, the third and sixth automatic valves V3, V6 are opened (S 20), and the composition in the transfer vessel 30 is supplied to the flow cell 70 by the pressure of nitrogen gas injected to the transfer vessel 30 (S 22), and the composition transferred to the flow cell 70 is recycled to the storage tank 10 through the sixth automatic valve V6. In this process, the rate at which the composition is recycled to the storage tank 10 can be adjusted by controlling the amount of the injected nitrogen gas by using the regulator R2 installed in nitrogen gas injection inlet. When the low-level sensor of the transfer vessel 30 stops sensing (S 24), the third and sixth automatic valves V3, V6 are closed to prevent the flow of the composition (S 26). The highest level sensor and the lowest level sensor in the transfer vessel 30 are provided to cope with the operation failure of the high-level sensor and the low-level sensor. As described above, while the composition in the storage tank 10 is passing through a flow cell 70, the concentration of at least one component of the composition is measured by using a near infrared spectrometer 80(S28), and the measured concentration of the component is outputted through the output unit 90, together with the composition's status (S 30).

Figure 4:
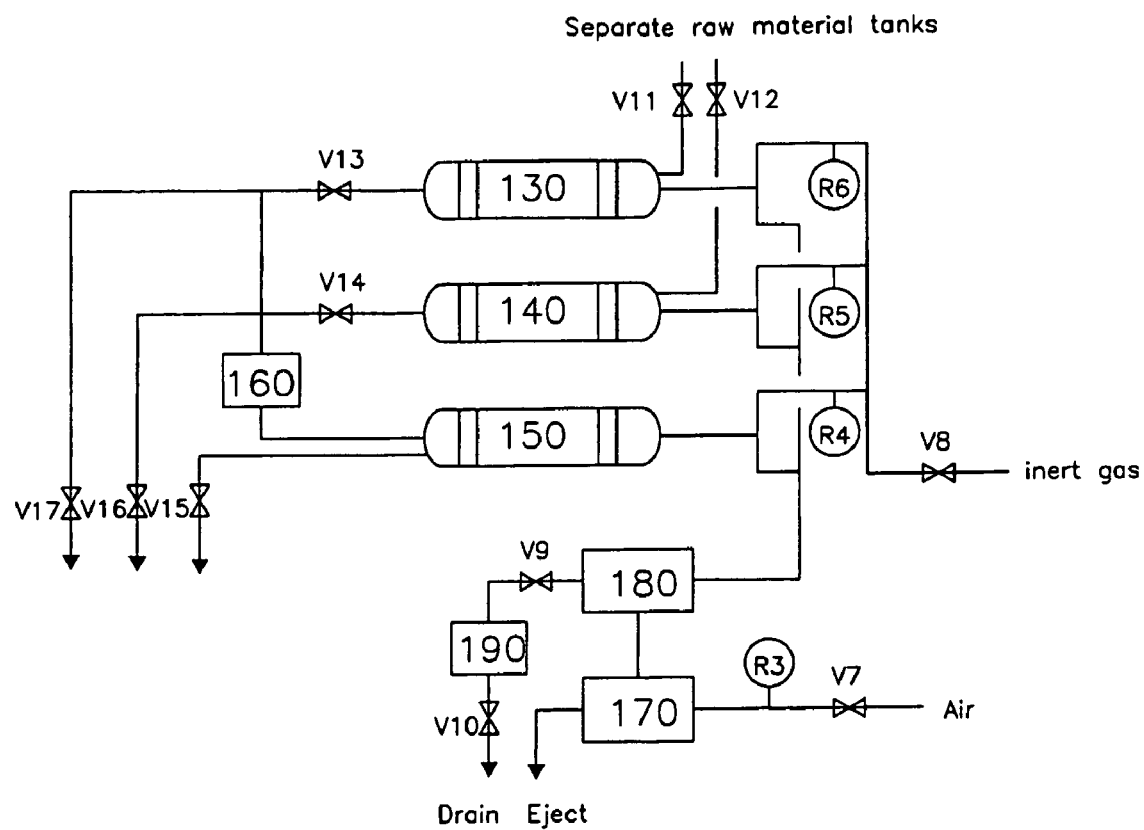
FIG. 4 is a block diagram of a component supplier, which is used in a system for controlling a composition according to an embodiment of the present invention.

FIG. 4 is a block diagram of the component supplier used in the system according to an embodiment of the present invention. The component supplier is an apparatus for supplying an additional solution or a deficient component to the storage tank 10 from a separate tank, when the concentration of at least one component of the measured composition is below the predetermined level. As show in FIG. 4, iii) the component supplier includes one or more automatic valves V11, V12, one or more addition tanks 130, 140 for temporarily retaining the composition injected through the automatic valves V11, V12, and for supplying the retained composition to the storage tank 10, and a vacuum reservoir 180 for vacuumizing the addition tanks 130, 140. The vacuum reservoir 180 is vacuumized, or is supplied with inert gas such as nitrogen gas. In case that the vacuum reservoir 180 is vacuumized, the deficient composition or component is supplied to the addition tanks 130, 140 from the separate raw material tanks (not shown). In case that the vacuum reservoir 180 is supplied with nitrogen gas, the composition or component to be added is transferred to the storage tank 10 from the addition tanks 130, 140 due to the pressure of nitrogen gas.

The component supplier can further include a vacuum ejector 170 for vaccumizing the vacuum reservoir 180 by injecting air thereto and ejecting air therefrom by the control of the seventh automatic valve V7. The amount of the air injected into the vacuum ejector 170 can be controlled by adjusting the third regulator R3 installed between the seventh automatic valve V7 and the vacuum ejector 170. Also, the component supplier can further include a drain transfer tank 190, which is connected to the vacuum reservoir 180, for retaining the composition overflowing the addition tanks 130, 140, in case that the excess composition is injected into the addition tanks 130, 140, the ninth automatic valve V9 for controlling the injection of the excess composition into the drain transfer tank 190, the tenth automatic valve V10 for controlling the ejection of the composition from the drain transfer tank 190, the eighth automatic valve V8 for injecting inert gas (for example, nitrogen gas) to the vacuum reservoir 180 and the fourth, fifth and sixth regulators R4, R5, R6 for controlling the amount of the nitrogen gas injected into the vacuum reservoir 180. At the end of the addition tanks 130, 140, various automatic valves V13-V17 for supplying the composition or component in the addition tanks 130, 140 to the storage tank 10 can be installed. In addition, a line mixer 160 for mixing the components in addition tanks 130, 140 and a mixing tank 150 for retaining the mixed solution can be further provided.

Figure 5:
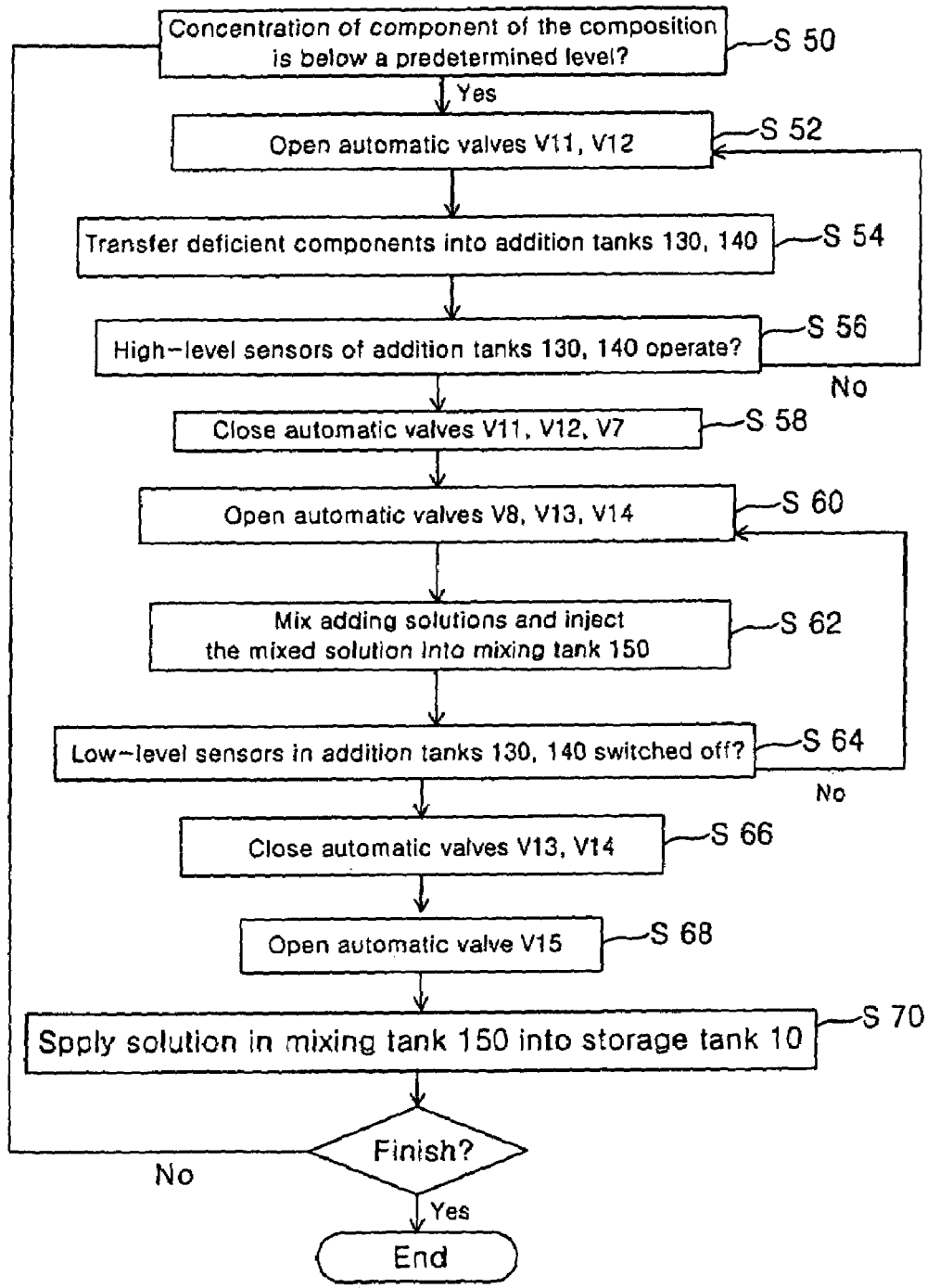
FIG. 5 is a flow chart for illustrating the operation of a component supplier, which is used in a system for controlling a composition according to an embodiment of the present invention.

By reference to FIG. 5, the operation of the component supplier is explained hereinafter. For example, when the concentrations of 2 components of the composition are below their respective predetermined level (S 50), the eleventh and twelfth automatic valves V11, V12 are opened (S 52), and consequently the deficient components are transferred into the addition tanks 130, 140 (S 54). When a high-level sensor of the addition tanks 130, 140 operates with the injection of the deficient components (S 56), the eleventh, twelfth and seventh automatic valves V11, V12, V7 are closed (S 58). And the eighth automatic valve V8 is opened to inject nitrogen gas, and the thirteenth and fourteenth automatic valves V13, V14 are opened (S 60) so that each of the adding solution passes through a line mixer 160 by the pressure of nitrogen gas, and consequently each of the adding solution is mixed and injected into the mixing tank 150(S 62), Then, when low-level sensors in the addition tanks 13, 14 are switched off (S 64), the thirteenth and fourteenth automatic valves V13, V14 are closed (S 66), and the fifteenth automatic valve V15 is opened (S 68), and the adding solution in the mixing tank 150 is supplied to the storage tank 10 by the pressure of nitrogen gas (S 70). According to the same method as described above, 3 or more compositions can be mixed and supplied by increasing the number of the addition tank to 3 or more. The rate at which the adding solution is transferred can be adjusted by controlling regulators R3 to R6 installed in an air injection inlet or a nitrogen gas injection inlet.

In the present invention, i) the composition circulator, ii) the composition analyzer, iii) the controller and iv) the component supplier can be manufactured in an independent cabinet device, respectively, and accordingly can be readily equipped in the existing or new process facilities. Also, by using only ii) the composition analyzer and iv) the component supplier, the function of measuring the concentration of the composition and the function of supplying the deficient components can be carried out in a simple manner. The cabinet, the tank, the automatic valves, the transfer vessel, the necessary line and so on, which constitutes the system of the present invention, can be made of stainless still such as SUS, polyvinylchloride(PVC), polyethylene(PE) and Teflon, according to the properties of the composition. In addition, a pump or a vacuum apparatus can be selectively used according to the properties of the composition to transfer the composition. When successively analyzing two or more compositions in two or more tanks, analysis can be performed time-effectively in real time by only receiving the information of currently analyzed tank from the tank controller 15. Also, in the present invention, only one near infrared spectrometer 80, one output unit 90 and one controller 100 can be used for two or more flow cells 70 for respectively receiving different compositions, which reduces the cost of equipment.

The system of the present invention preferably further equipped with a leakage sensor for sensing the leakage of the composition, for example, due to the problem on a joint part of Teflon tube or any other reason. By installing the leakage sensor, the stability of the system can be improved. In addition, various alarms for alarming the problem on sensors, concentrations of components of analyzed composition, concentrations of impurities, malfunction of the near infrared spectrometer, and so on, can be readily equipped on the system of the present invention. The alarm signals can be transmitted to the tank controller 15, and be checked by a user in a separate control room.

As described above, the system and the method for controlling the composition for a lithography process of the present invention, (1) do not cause any change or degeneration in the analyzed composition, (2) can analyze two or more components with one flow cell and can analyze the various compositions by using two or more flow cells, (3) do not require several conventional analysis apparatuses, and do not generate waste water because the system can analyze the multi-component composition with a near infrared spectrometer, (4) can selectively analyze the composition in the currently used tank in a lithography process, and can manage the composition's status, and (5) can transfer the composition either by a pump or a vacuum apparatus according to the property of the analyzed composition.

The invention claimed is:

1. A system for controlling a composition for a lithography process in real time, comprising:
    a composition circulator for withdrawing the composition from a storage tank retaining the composition for a lithography process, and for recycling the withdrawn composition to the storage tank, through a flow cell;
    a composition analyzer for measuring an absorbance of the composition passing through the flow cell, and for calculating the concentration of at least one component of the composition from the measured absorbance;
    a component supplier for supplying a deficient component to the storage tank when a concentration of the deficient component is below a predetermined level; and
    a controller for controlling the component supplier to adjust the concentration of each component of the composition according to the absorbance,
    wherein the composition circulator comprises:
    a first automatic valve, which is installed on the storage tank retaining the composition, for withdrawing the composition from the storage tank;
    a transfer vessel for receiving the composition withdrawn from the storage tank through the first automatic valve, and for transferring the received composition to the flow cell; and
    a vacuum reservoir for vacuumizing the transfer vessel,
    wherein the composition circulator further includes a vacuum ejector for vacuumizing the vacuum reservoir by receiving air and ejecting air therefrom according to the control of a second automatic valve.

2. The system for controlling a composition for a lithography process of claim 1, wherein the vacuum reservoir is vacuumized or is supplied with inert gas, and when the vacuum reservoir is vacuumized, the composition is supplied to the transfer vessel from the storage tank, and when inert gas is supplied to the vacuum reservoir, the composition is transferred to the flow cell from the transfer vessel due to the pressure of the inert gas.

3. The system for controlling a composition for a lithography process of claim 1, wherein the composition analyzer includes the flow cell, through which the composition to be analyzed passes; an optical fiber for irradiating light to the composition for measuring absorbance of the composition; and a near infrared spectrometer for measuring the absorbance of the composition.

4. A method for controlling a composition for a lithography process in real time, comprising the steps of:
    transferring a composition in a storage tank for a lithography process to a transfer vessel of a depressurized condition;
    transferring the composition in the transfer vessel to a flow cell by injecting inert gas to the transfer vessel;
    measuring a concentration of at least one component of the composition by measuring an absorbance of the composition while the composition passes through the flow cell;
    recycling the composition from the flow cell to the storage tank;
    transferring a deficient component of the composition into an addition tank; and
    supplying the deficient component in the addition tank into the storage tank.

5. The method for controlling a composition for a lithography process of claim 4, wherein the number of the deficient component is two or more, and the method further includes the step of mixing the deficient components.

6. The method for controlling a composition for a lithography process of claim 4, wherein the method includes the steps of outputting the concentration of at least one component of the composition and the composition's status.

7. A system for controlling a composition for a lithography process in real time, comprising:
    a composition circulator for withdrawing the composition from a storage tank retaining the composition for a lithography process, and for recycling the withdrawn composition to the storage tank, through a flow cell;
    a composition analyzer for measuring an absorbance of the composition passing through the flow cell, and for calculating the concentration of at least one component of the composition from the measured absorbance;
    a component supplier for supplying a deficient component to the storage tank when a concentration of the deficient component is below a predetermined level; and
    a controller for controlling the component supplier to adjust the concentration of each component of the composition according to the absorbance,
    wherein the composition circulator comprises:
    a first automatic valve, which is installed on the storage tank retaining the composition, for withdrawing the composition from the storage tank;
    a transfer vessel for receiving the composition withdrawn from the storage tank through the first automatic valve, and for transferring the received composition to the flow cell; and
    a vacuum reservoir for vacuumizing the transfer vessel,
    wherein the composition circulator further includes a drain transfer tank, which is connected to the vacuum reservoir, for receiving the composition overflowing from the transfer vessel when the excess amount of the composition is injected into the transfer vessel.

8. A system for controlling a composition for a lithography process in real time, comprising:
    a composition circulator for withdrawing the composition from a storage tank retaining the composition for a lithography process, and for recycling the withdrawn composition to the storage tank, through a flow cell;
    a composition analyzer for measuring an absorbance of the composition passing through the flow cell, and for calculating the concentration of at least one component of the composition from the measured absorbance;
    a component supplier for supplying a deficient component to the storage tank when a concentration of the deficient component is below a predetermined level; and
    a controller for controlling the component supplier to adjust the concentration of each component of the composition according to the absorbance,
    wherein the component supplier includes one or more addition tanks for temporarily retaining the composition and for supplying the retained composition to the storage tank; and a vacuum reservoir for vacuumizing the addition tanks,
    wherein the component supplier further includes a line mixer for mixing the components in the addition tanks; and a mixing tank for retaining the mixed solution.

* * * * *